(12) United States Patent
Harris et al.

(10) Patent No.: US 7,313,947 B2
(45) Date of Patent: Jan. 1, 2008

(54) CORROSION SENSING MICROSENSORS

(75) Inventors: Steven J Harris, Filton (GB); Michael C Hebbron, Filton (GB); Ian M Sturland, Filton (GB)

(73) Assignee: Bae Systems PLC, London (GB)

( * ) Notice: Subject to any disclaimer, the term of this patent is extended or adjusted under 35 U.S.C. 154(b) by 0 days.

(21) Appl. No.: 10/529,056

(22) PCT Filed: Sep. 30, 2003

(86) PCT No.: PCT/GB03/04209

§ 371 (c)(1),
(2), (4) Date: Mar. 24, 2005

(87) PCT Pub. No.: WO2004/031739

PCT Pub. Date: Apr. 15, 2004

(65) Prior Publication Data
US 2006/0162431 A1 Jul. 27, 2006

(30) Foreign Application Priority Data
Oct. 1, 2002 (GB) .................................. 0222658.7

(51) Int. Cl.
*G01N 27/20* (2006.01)
(52) U.S. Cl. .......................................... 73/86; 324/71.2
(58) Field of Classification Search .................... 73/86; 324/71.2
See application file for complete search history.

(56) References Cited

U.S. PATENT DOCUMENTS

| 4,780,664 | A | * | 10/1988 | Ansuini et al. | ............. | 324/700 |
|---|---|---|---|---|---|---|
| 5,306,414 | A | | 4/1994 | Glass et al. | | |
| 5,338,432 | A | | 8/1994 | Agarwala et al. | | |
| 5,446,369 | A | | 8/1995 | Byrne et al. | | |
| 6,516,785 | B1 | * | 2/2003 | Nakada et al. | ............... | 123/494 |
| 2003/0029232 | A1 | | 2/2003 | Dinwiddie et al. | | |

FOREIGN PATENT DOCUMENTS

| JP | 59159061 A | 9/1984 |
|---|---|---|
| JP | 59180433 A | 10/1984 |
| JP | 01197629 A | 8/1989 |
| JP | 07113740 A | 5/1995 |
| WO | 01/81897 | 11/2001 |

OTHER PUBLICATIONS

C.G. Moore, et al, "Instrumentation for Measurement of the Effectiveness of Vapor Corrosion Inhibitors" National Association of Corrosion Engineers, Corrosion '95, Mar. 1995, pp. 1-8.

* cited by examiner

*Primary Examiner*—Hezron Williams
*Assistant Examiner*—Paul M West
(74) *Attorney, Agent, or Firm*—Nixon & Vanderhye P.C.

(57) ABSTRACT

A microsensor for detecting corrosive media acting on a bulk metallic material when mounted in situ adjacent a location in the bulk metallic material. The microsensor includes a plurality of corrosion sensors (4A, 4B, 4C) exposed to the corrosive media, each having corrosive tracks formed from a patterned conductive thin film. The different sensors have different characteristics, such as track width, track thickness, track composition, surface type, sensor type, etc. so as to provide the sensors with different sensitivities, corrosion indications and lifetime characteristics. Such microsensor arrangements provide improved corrosion detection at high degrees of miniaturisation.

11 Claims, 3 Drawing Sheets

CORROSION SENSING MICROSENSORS

This application is the US national phase of international application PCT/GB03/04209 filed 30 Sep. 2003 which designated the U.S. and claims priority of GB 0222658.7, filed 1 Oct. 2002, the entire contents of each of which are hereby incorporated by reference.

This invention relates to microsensors for detecting corrosive media acting on a metallic material when mounted in situ adjacent a location in the metallic material.

Corrosion is a problem which leads to high maintenance and repair overheads in many different industries. The paper "Naval Aviation Corrosion Challenges and Solutions", Dale L. Moore, Corrosion 2000, paper 00270 (NACE, Orlando, USA, 2000) describes the problem areas in aircraft component corrosion and classifies corrosion types found in the aircraft industry.

Various different methods of detecting corrosion in a metallic material are known. The paper "Corrosion Detection and Monitoring—a Review", Vinod S. Agarwala, Siri Ahmad, Corrosion 2000, paper 00271 (NACE, Orlando, USA, 2000) describes various of the known methods, including visual methods, ultrasonic and acoustic methods, radiographic methods, thermal imaging, electromagnetic methods, electrical resistance measurement, and electrochemical methods. It describes a commonly used type of corrosion sensing, referred to as the electrical resistance probe method. In this case a sample of the material being monitored has its electrical resistance monitored. As the metal corrodes its cross section reduces and the resistance increases. In a practical embodiment of this technique the metal sample is made long and thin in order to optimise the resistance change to the thickness loss by corrosion. In this sensitive configuration the sensor is also highly sensitive to temperature changes by virtue of the material's temperature coefficient of resistivity. This is often overcome by using a second sample of the material of identical dimensions and temperature but protected from corrosion. Even when all these features are accommodated this sensor type is poor when the corrosion is at all localised, e.g. exfoliation, intergranular, pitting, crevice or stress corrosion. Under these conditions of degradation the resistance change is not proportional to extent of corrosion. Indeed it may not change sufficiently to allow problematic corrosion to be reliably detected. Localised types of corrosion cause significant problems for some types of metallic materials such as aluminium alloys.

The paper "Multi-layer Galvanic Cell for Next Generation Corrosion Sensors", M. D. Jaeger, B. R. Pilvelait, P. J. Magari, Corrosion 2000, paper 00302 (NACE, Orlando, USA, 2000) describes a galvanic sensor with a multilayer geometry which is to be mounted in situ adjacent a location in a metallic material to be monitored and provides advantages in sensitivity and lifetime. The sensor measures the presence of an electrolyte, e.g. moisture in the area of the sensor, but not actual corrosion of the metallic material.

U.S. Pat. No. 5,338,432 describes galvanic microsensors which use patterned thin metallic foils bonded to a non-conductive substrate. The sensors described include various alternative arrangements of interdigitated tracks of different metallic materials.

U.S. Pat. No. 6,383,451 describes a thin film electric resistance sensor which includes a plurality of corrosive tracks exposed to corrosive media, running between two corrosion-protected common terminals. The detector described is sensitive to slight corrosion caused by pitting corrosion, however the current drain remains relatively high. In particular for corrosion monitoring in situ, it would be desirable to reduce the current drain in order to provide a longer battery lifespan; this is particularly important when a microsensor is to be mounted in a relatively inaccessible location and access thereto, for example for battery replacement, is to be avoided to as great an extent as possible. It would also be desirable to further improve the sensitivity and accuracy of the microsensor in detecting location-specific corrosion.

In accordance with one aspect of the present invention there is provided a microsensor for detecting corrosive media acting on a metallic material when mounted in situ adjacent a location in the metallic material, the microsensor including a plurality of different corrosion sensors, each said sensor having at least a part formed from a patterned conductive thin film and the different sensors being arranged to be differently influenced by corrosive media in an area in which the unit is mounted, said microsensor providing a separate output derived from each of said sensors respectively.

The present invention provides a highly miniaturised microsensor which can detect corrosion with high accuracy and reliability, whilst a relatively long lifetime of the microsensor is achievable.

Further aspects, features and advantages of the invention will become apparent from the following description of preferred embodiments of the invention given, by way of example, with reference to the accompanying drawings, wherein.

Various different embodiments of microsensor in accordance with the invention will now be described. The microsensors include corrosive tracks which mimic the corrosive characteristics of a bulk metal material, such that when placed in situ adjacent a location in a bulk metal material component, the effects of exposure to corrosive media measured by the microsensor reflect the effects of exposure of the bulk metal to the same corrosive media. The microsensors may be mounted in various locations and manners, for example by mounting between the plates of a joint between components, by adhesion to a component using a Mylar™ foil, etc. Once mounted, the microsensors may be coated with paint or another type of coating which similarly covers the bulk metal material.

Figure 1:
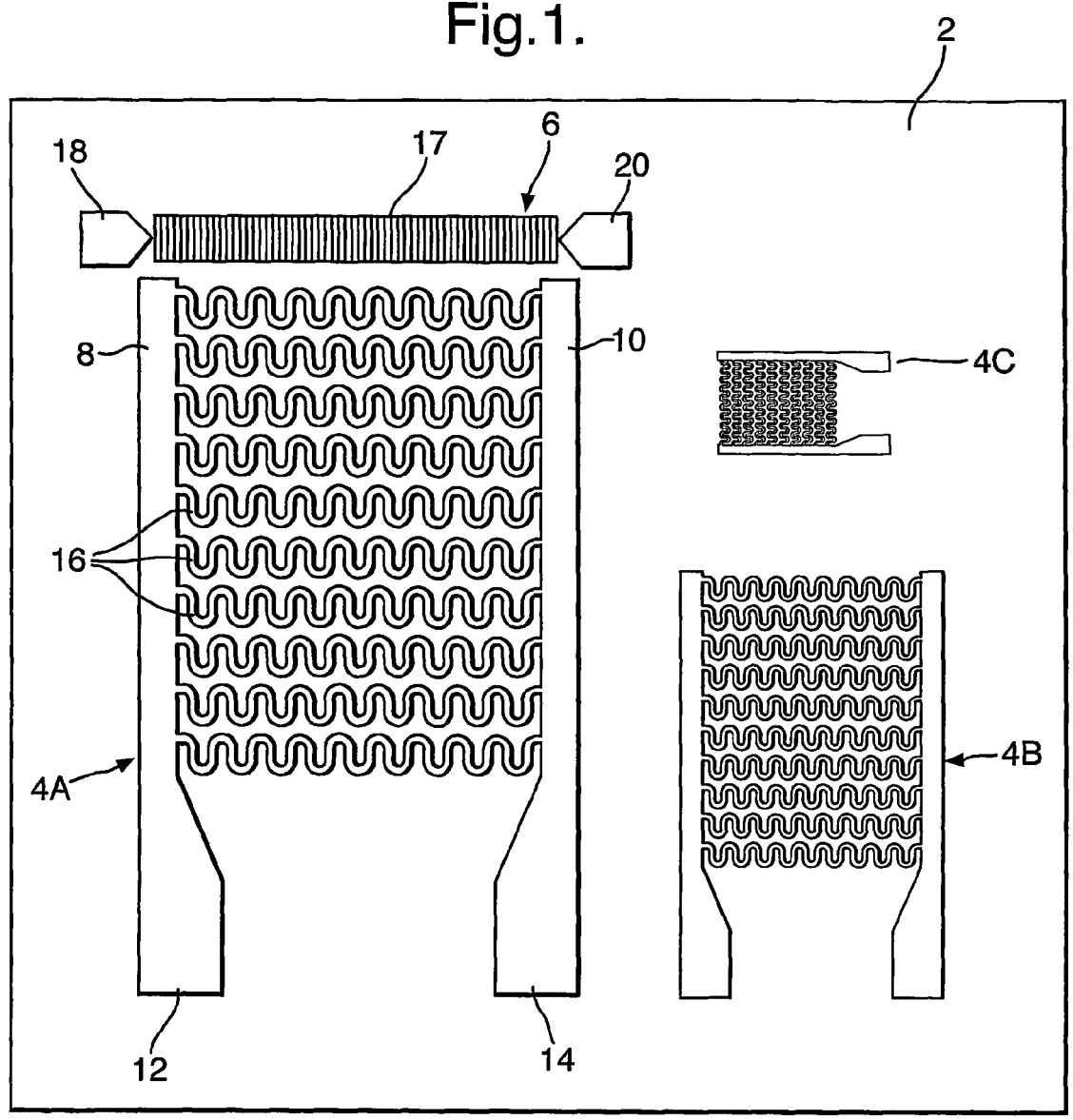
FIG. 1 shows a microsensor arranged in accordance with a first embodiment of the invention, in plan view.

FIG. 1 shows a microsensor element including a plurality of different corrosion sensors according to a first embodiment of the invention. The microsensor element includes a planar substrate 2 having an insulating surface provided for example by a layer of silicon oxide formed on a silicon base. The substrate 2 supports three thin film linear polarisation resistance (LPR) corrosion sensors 4A, 4B, 4C formed as thin film metallic patterns, and a thermocouple sensor 6 also formed as thin film metallic patterns. Each of the three corrosion sensors is formed of similar thin film patterns having similar geometries, except is formed of a different scale to the scale of the other corrosion sensors. For the avoidance of unnecessary repetition, the parts and functioning of only the largest corrosion sensor 4A are described in detail below, however it should be understood that each of the other corrosion sensors 4B, 4C has elements which are similar in arrangement and function to corresponding elements to be described, and the description of such elements should be taken to apply in relation to the other corrosion sensors also.

The largest corrosion sensor 4A includes two common terminals 8, 10 formed side-by-side in parallel strips on the substrate 2, ending in respective connector stubs 12, 14, across which an output signal is sensed. The common terminals 8, 10 may be made of a metal which is highly resistant to corrosion, such as gold or platinum, and/or may be covered in a protective thin film to prevent exposure of the common terminals 8, 10 to corrosive media.

Between the common terminals 8, 10, a plurality of conductive thin film corrosive tracks 16 are formed. The corrosive tracks 16 are not covered by a protective thin film, and are thus exposed to corrosive media, when the microsensor is in use, to a similar degree to which the bulk metallic alloy material, adjacent to which the microsensor is mounted, is exposed in the mounting location.

Figure 2:
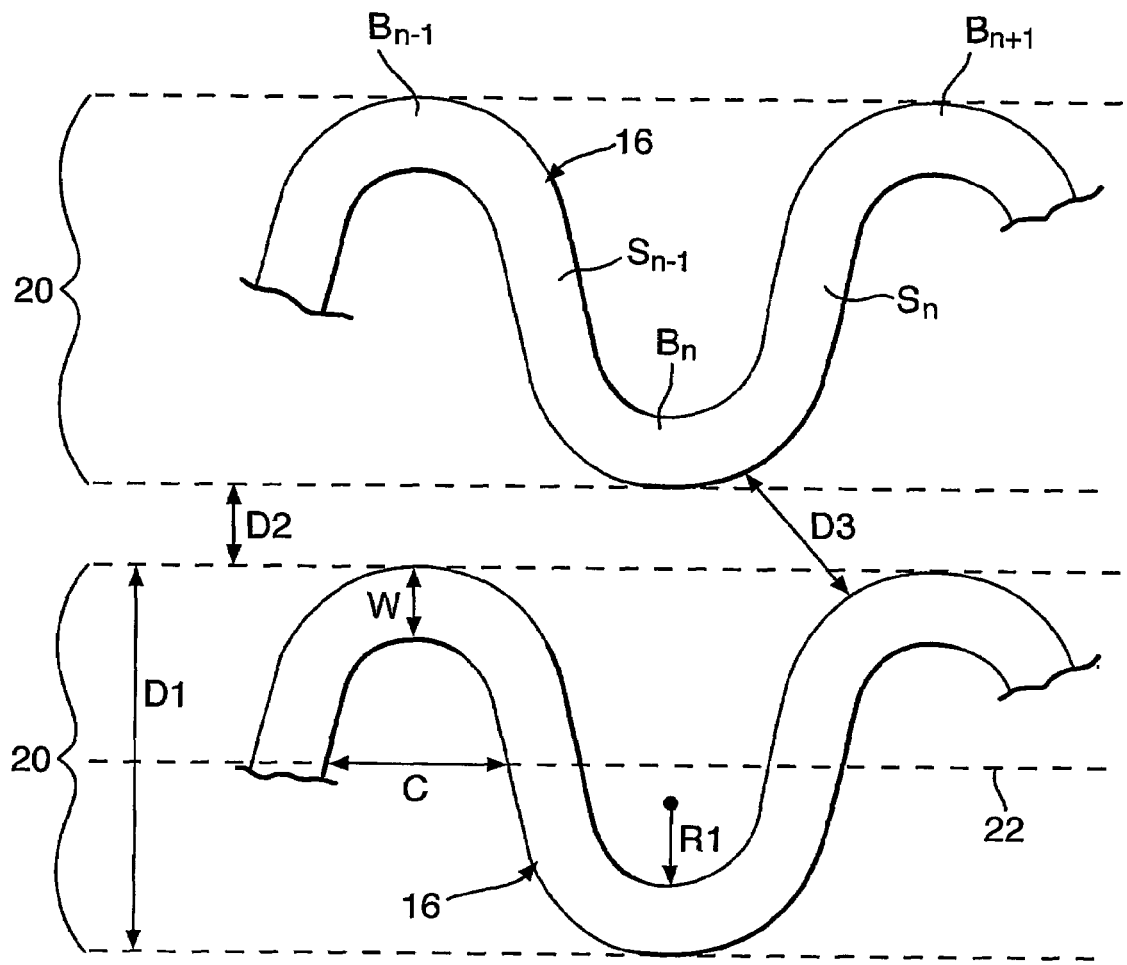
FIG. 2 shows a more detailed plan view of the formation of corrosive tracks in the corrosion sensors of the microsensor shown in FIG. 1.

FIG. 2 shows a more detailed plan view of the formation of the corrosive tracks 16. Each corrosive track has a width W which is substantially constant, preferably to within 10% of the width, across its length. As an exemplary value, the width W of each corrosive track may be selected to be in the region of 100 μm in width.

Each corrosive track 16 is formed to meander across a separate surface portion, in this embodiment one of a set of linear corridors 20, between the common terminals 8, 10. The track 16 extends fully across the corridor 20 in which it meanders. The corridors 20 each have a similar width D1 and are separated by a distance D2 such that the minimum separation D3 between adjacent corrosive tracks is preferably at least as great as the track width W. Each corrosive track 16 has a periodically repeating serpentine shape within the linear corridor. As can be seen in FIG. 2, the corrosive tracks 16 are formed from alternately inverted generally U-shaped bends B1, B2 . . . Bn . . . connected by track sections S1, S2 . . . Sn . . . spanning the centreline 22 of a corridor 20. The bends are alternately of opposite curvature. Each bend has a minimum radius of curvature R which is preferably greater than half the track width W. The spanning sections S1, S2 . . . Sn . . . are spaced from each other such that the sides of adjacent spanning sections are spaced by a distance C at the centreline, which distance is preferably greater than the track width W.

As a result of the serpentine shape of the corrosive track 16, the track gradually changes in direction, so that, using the centre line 22 as a reference axis, a track section of a positive or negative gradient relative to the centre line 22 is followed by a track section of an opposite gradient relative to the centre line 22, the two sections being to each side of a bend of the corrosive track. The gradients alternately vary as the track is followed through each bend. The serpentine paths thus resemble a periodic waveform.

By providing a serpentine path such as that described, the track length is increased without the need to increase the microsensor dimensions correspondingly, thus aiding miniaturisation. The sensitivity of the sensor is thus increased due to the increased track length and the current drain reduced. By using gradual bends having a minimum radius of curvature which is greater than half the track width as described, discrete or excessively sudden changes in direction of the path of the corrosive tracks, for example by the formation of right angles in the track paths, are avoided. It has been found that accelerated corrosion phenomena occur at such points in the track paths, which undesirably produce resistance variations which do not accurately reflect the state of corrosion of the component being monitored.

By maintaining at least a predetermined distance D3 between adjacent tracks, a predetermined minimum radius of curvature R at the bends, and at least a predetermined distance C between the adjacent track sections at the centre line, all track sections, including track sections within a single track and track sections within adjacent tracks, are well-spaced across the sensor. Preferably, no two adjacent track sections have sides spaced from each other by less than the track width W. In this way, corrosion effects are produced which more closely mimic the corrosion effects in the bulk alloy.

When mounted in situ, the effects of corrosion are monitored by intermittently passing a constant current across the common terminals and sensing the voltage response. After a period of exposure to corrosive media, whilst initially the tracking is fully intact and fully conductive, corroded track becomes gradually more resistive due to loss of conductive cross-sectional area and finally becomes insulating after corrosion affects at least one part of the track fully across its entire width. Different of the tracks may be affected differently by unrepresentative corrosive phenomena or other phenomena such as percussive damage, but by using a number of tracks, preferably at least four or more, connected in parallel, the response of the sensor more reliably reflects the effects of corrosion in the adjacent bulk metal.

The resistance thermometer 6 is made of a conductive material which is corrosively inert, such as platinum. The resistance thermometer 6 includes a tightly-concertinaed sensing section 17 which provides well-behaved measurable variations in resistivity with temperature, formed between connector stubs 18, 20. Since rates of corrosion are highly temperature-dependent, the output from the resistance thermometer can be used in combination with the output from the corrosion sensor to provide more accurate corrosion state prediction for the bulk alloy material being monitored.

The microsensor may also include other types of sensor, not shown, for measuring parameters which can have an effect on corrosion rates, such as an airflow sensor arranged for measuring airflow in the area in which the unit is mounted. Such an airflow sensor may be formed as thin film patterns of conductive strips, made of a material having a high temperature coefficient of resistivity, which are spaced in a direction in which airflow is to be sensed; variations in resistance of the strips indicate levels of airflow.

The second corrosion sensor 4B is in this embodiment formed of a scale which is half or less of the scale of the first and largest corrosion sensor 4A. The third corrosion sensor 4C is in this embodiment formed of a scale which is half or less of the scale of the second corrosion sensor 4B. More pronounced variations in scale are envisaged in a single microsensor element, for example a scale variation between any two microsensors may such that one microsensor is one tenth or less of the scale of the other microsensor. The variations in sensor scale provide sensors with corrosive tracking of different widths in each sensor. By including the differently scaled sensors in a single microsensor unit the microsensor unit has a plurality of sensor outputs, derived from each sensor respectively, of different sensitivities to corrosion and with different sensor lifetimes. A sensor having a relatively small track width will be more sensitive but have a relatively small lifetime; the output from such a relatively small sensor may be used for monitoring corrosion during the early part of the life of the microsensor. Once the tracking of the relatively small sensor has degraded a sensor having a larger track width may be used to continue corrosion monitoring at a lower sensitivity during a subsequent period. When three or more sensors of different scales are used, once the output of the next smallest sensor has degraded a sensor having a larger track width may be used to continue corrosion monitoring at a still lower sensitivity during one or more further subsequent periods.

At any stage, corrective or preventive action may be taken as desired, in view of any perceived level of risk caused by the amount of corrosion detected at the location at which the corrosion is being monitored.

Figure 3:
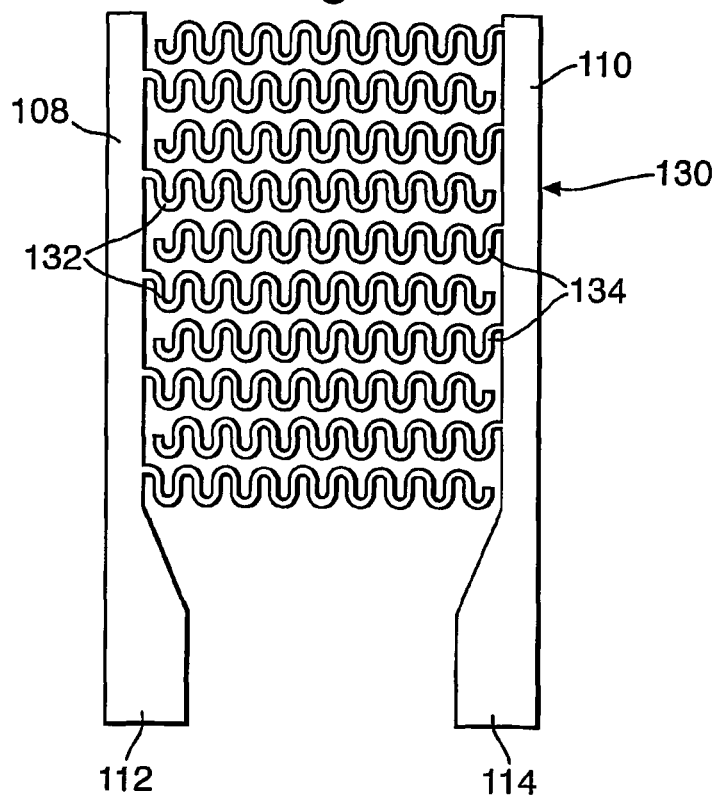
FIG. 3 shows a galvanic corrosion sensor conductive pattern arrangement in accordance with an embodiment of the invention, in plan view.

FIG. 3 shows an alternative sensor pattern arrangement, for a galvanic corrosion sensor 130 arranged in accordance with one embodiment of the invention. One or more of the resistive sensors shown in FIG. 1 may be replaced with a galvanic corrosion sensor arranged as shown in FIG. 3. For the avoidance of unnecessary repetition, elements which are similar in arrangement and function to corresponding elements shown in FIG. 1 are referenced with the same numerals in FIG. 3, except incremented by 100, and the previous description of such elements should be taken to apply here.

In this embodiment, the corrosion sensor 130 is in the form of a galvanic corrosion sensor having interdigitated thin film tracks 132, 134 formed of different metallic materials and producing a measurable variation in galvanic voltage in response to exposure to an electrolyte. The thin film tracks 132, 134 are not covered by a protective thin film and are thus exposed to an electrolyte, which is a corrosive medium such as moisture, when the microsensor is in use, to a similar degree to which the bulk metallic alloy material, adjacent to which the microsensor is mounted, is exposed in the mounting location.

The thin film tracks include a first set of thin film tracks 132 and a second set of thin film tracks 134. The first set are made from a first metallic material connected to a first common terminal 108 and not connected to the second common terminal 110. The second set of thin film tracks 134 are made from a second, different, metallic material connected to the second common terminal 110 and not connected to the first common terminal 108. Preferably, the first set of tracks 132 are formed from a corrosive material mimicking the bulk metal for which the microsensor is to be used to monitor corrosion, and the second set of tracks 134 are formed from a relatively corrosively inert metal such as gold or platinum. Thus, a galvanic voltage is generated between the common terminals by the sets of corrosive tracks 132 and the set of non-corrosive tracks 134, which is measurable to provide an indication of time of exposure and amount of exposure to the electrolyte in the bulk material.

The tracks 132, 134 are formed in the patterns described above in relation to FIG. 2 in order to improve the performance of the sensor as described above.

Figure 4:
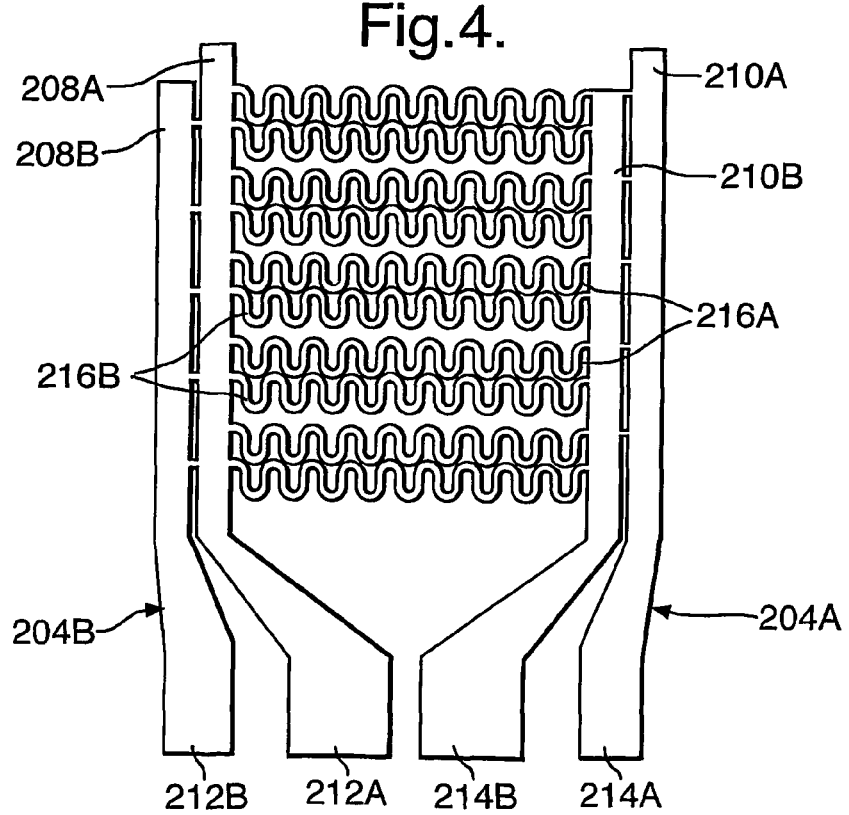
FIG. 4 shows a referenced corrosion sensor pattern arrangement in accordance with an embodiment of the invention, in plan view.

FIG. 4 shows an alternative sensor pattern arrangement, for a referenced corrosion sensor 130 arranged in accordance with one embodiment of the invention. One or more of the resistive sensors shown in FIG. 1 may be replaced with a referenced corrosion sensor arranged as shown in FIG. 4. For the avoidance of unnecessary repetition, elements which are similar in arrangement and function to corresponding elements shown in FIG. 1 are referenced with the same numerals and further referenced A or B respectively in FIG. 4, except incremented by 200, and the previous description of such elements should be taken to apply here.

In this embodiment, a corrosion sensor 204B having a similar form to the resistive corrosion sensor described in relation to FIG. 1 formed with a reference sensor 204A which takes substantially the same form and is made of substantially the same material or materials as the corrosion sensor 204B, but is covered by a protective thin film layer and is thus not exposed to corrosive media when the microsensor is in use. In manufacture, the reference sensor 204A is first laid down and formed, followed by the protective layer, followed by the corrosion sensor 204B.

The corrosion sensor 204B is formed in an overlapping arrangement on top of the reference sensor. The function of the reference sensor 204A is to provide an output which is independent of corrosion but which has a virtually identical temperature-dependence in resistivity as the corrosion sensor 204B, due to its similar patterning and composition. The output from the reference sensor 204A can thus be used to balance out any temperature dependence in the output of the corrosion sensor 204B in a simple manner. By arranging the two sensors in an overlapping manner, rather than side-by-side, the temperature of the corrosion sensor 204B and the reference sensor 204A are more closely matched, in particular when mounted in locations subject to relatively large temperature gradients. Hence, the function of the reference sensor 204A is improved. Furthermore, miniaturisation of the microsensor element is improved.

The two sensors 204A, 204B are arranged with a slight offset, and the corrosive tracks 216B and the corresponding tracks 216A are formed with a greater pitch. Thereby, the corrosive tracks 216B of the corrosion sensor are not formed on the surface of the protective film covering the corresponding tracks 216A of the reference sensor; this avoids degradation of the uniformity of the corrosive tracks 216B due to variations in surface height of the protective layer due to the tracks 216A underneath. In this embodiment, the number of tracks in each sensor is half that of the sensor shown in FIG. 1, which provides a microsensor element of similar size, however larger numbers of elements may be provided by increasing the length of the common terminals 208A, 210A; 208B, 210B.

Note that, in relation to FIGS. 1, 3 and 4, thin film wiring patterning, or other types of wiring, connecting the sensor connector stubs in a microsensor unit, although not shown, is to be understood to be added. Further, protective coatings are not shown in the Figures, although, as described above, may be used to selectively protect parts of the surface of the microsensor element.

In particular envisaged applications, the bulk metal material to be mimicked is a metallic alloy and in such cases the material used for the corrosive tracks in each of the above-described embodiments is preferably an alloy having alloying constituents in similar proportions to the respective bulk alloy being mimicked. It has been found that the proportion of each alloying constituent of the track material is generally preferred to be accurate within 3%, more preferably within 1%, of the total constituents of the bulk alloy. Constituents having a proportion of less than 1% of the bulk alloy may either be present in a similar proportion, or omitted.

In preferred embodiments, in which the microsensor is to be used in a health monitoring system for aircraft, the corrosive tracks are made of an aluminium alloy, such as an aluminium copper alloy, an aluminium silicon alloy, an aluminium silicon copper alloy, etc. In particular, the material used for the corrosive tracks is preferably an alloy which closely resembles in composition one of the aluminium alloys used in the aviation components.

In a first example the track alloy is an aluminium-copper alloy having a copper constituent proportion forming in the region of 2% to 8%, preferably approximately 5%, of the mass of the alloy, such as a 2000 series aluminium alloy.

In a second example the track alloy is an aluminium-silicon alloy having a silicon constituent proportion forming in the region of 5% to 20%, preferably approximately 12%, of the mass of the alloy, such as a 4000 series aluminium alloy.

In a third example the track alloy is an aluminium-magnesium alloy having a magnesium constituent proportion forming in the region of 2% to 8%, preferably approximately 5%, of the mass of the alloy, such as a 5000 series aluminium alloy.

In a fourth example the track alloy is an aluminium-magnesium-silicon alloy having magnesium and silicon proportions each forming in the region of 0.3% to 1.2% of the mass of the alloy, such as a 6000 series aluminium alloy.

In a fifth example the track alloy is an aluminium-zinc alloy having a zinc constituent proportion forming in the region of 2% to 8%, preferably approximately 5%, of the mass of the alloy, such as a 7000 series aluminium alloy.

In a sixth example the track alloy is an aluminium-lithium alloy having a lithium constituent proportion forming in the region of 1% to 4%, preferably approximately 2%, of the mass of the alloy, such as an 8000 series aluminium alloy.

Note that alloying constituents other than those specifically mentioned in each example above, and in lesser proportions to those specifically mentioned, may also be present in the alloys from which the tracks are made, particularly if present in the bulk alloys to be mimicked. These other alloying constituents may include one or more of magnesium, copper, manganese, silicon, iron, zinc, lithium, titanium, chromium, vanadium, zirconium, etc.

The thin film layers from which the corrosive tracks are made is preferably deposited on the substrate by sputtering. In order to further improve the degree to which the corrosive characteristics of the thin film tracks mimic the bulk alloy, the thin film layer is preferably annealed following sputtering to encourage growth of metallic grains within the thin layer to produce a thin film which is essentially a two-dimensional array of metallic grains. Enhancing the grain size after sputtering by annealing enhances the capability of the sensors to specifically detect localised corrosion, at the early stages of its growth. Since localised corrosion initiates at specific sites such as grain boundaries, specific intermetallic phases etc, production of thin films of metal alloys with similar compositions of the intermetallic phases and grain boundaries of the bulk metal alloys concerned enhances detection of such localised corrosion. By subsequent photolithographic patterning, the films are structured into track forms, as described above, that give a desired sensitivity to such corrosion.

The thickness of the corrosive tracks is selected in accordance with the material from which the tracks are formed and the type of application for the microsensor. For example, for monitoring components in a marine environment the rate of corrosion is relatively high, and therefore a relatively thick film is used, for example, in the case of an aluminium alloy, corrosive tracks in the region of 50 μm to 500 μm in thickness are used. However, for other applications in which the environment in which the microsensor is to be placed is less corrosive, higher sensitivity to corrosion is required, and therefore thinner films are used to form the corrosive tracks. In the case of monitoring non-marine aircraft components, the thickness of the corrosive tracks is preferably between 0.5 μm and 10 μm, for example approximately 1.5 μm.

The above-described geometries of the corrosive tracks may be used at any point in a range of miniaturisation scales. A track width of approximately 1 μm is possible, and highly sensitive in the range of scales envisaged. However, such a track width will produce a sensor which is generally too sensitive for practical corrosion sensing applications. Track widths of up to 1 mm are envisaged. Preferred track widths fall within the range 20 μm to 500 μm.

In one embodiment, not shown in the Figures, at least two of the different sensor configurations shown in FIGS. 1, 3 and 4 are formed on a single substrate, so as to provide a microsensor unit having a plurality of sensor outputs giving different indications of corrosion in a single location. For example, a galvanic corrosion sensor as described may be included to provide time-of-wetness data whilst a resistive corrosion sensor may be used to provide an indication of actual corrosion which has been caused by the presence of corrosive media in the mounting location.

In a yet further embodiment, not shown in the Figures, sensors having tracking arranged as described and of a plurality of different thicknesses are formed on a single substrate and included in a single microsensor unit, so as to provide a microsensor unit having a plurality of sensor outputs giving different sensitivities to corrosion and different sensor lifetimes.

In a yet further embodiment, not shown in the Figures, sensors having tracking arranged as described and of a plurality of different metallic compositions, each preferably sharing at least the main metallic constituent of the bulk alloy being monitored, of different corrosivities are formed on a single substrate and included in a single microsensor unit, so as to provide a microsensor unit having a plurality of sensor outputs giving different sensitivities to corrosion and different sensor lifetimes. For example, in this case for monitoring aluminium alloy components, a first sensor having tracking made of a material which is relatively corrosive, such as an aluminium-silicon-copper alloy, may be included for higher sensitivity to corrosion but have a smaller lifetime, and a second sensor having tracking made of a less corrosive material such as substantially pure aluminium may be included for longer lifetime corrosion detection at a lower sensitivity. A third sensor having tracking made of a material having an intermediate corrosivity such as an aluminium-silicon alloy may also be included for medium lifetime corrosion detection at a medium sensitivity. The different tracks may also have different widths to provide preferred sensitivity and lifetime characteristics.

In a yet further embodiment, not shown in the Figures, sensors having tracking arranged as described and having a plurality of different surface types, for example one may be provide with a hydrophilic or hydrophobic surface treatment, to provide tracking of different sensitivities and lifetimes. The different sensors are formed on a single substrate and included in a single microsensor unit, so as to provide a microsensor unit having a plurality of sensor outputs giving different sensitivities to corrosion and different sensor lifetimes.

The corrosion microsensors described herein are located on various different components of a multi-component apparatus, such as an aircraft, to form a corrosion sensing system, which itself is part of a health monitoring system for the apparatus. Typically, the components of the apparatus will be formed from different metal alloys, in particular, in the case of an aircraft, from different aluminium alloys such as the examples given above. One aspect of the invention is that a plurality of different corrosion microsensors, each having a set of corrosive tracks made of different metal alloy compositions mimicking the different component material compositions, are mounted adjacent locations in the respective corresponding components to form part of the corrosion sensing system for the apparatus.

A corrosion sensing system arranged in accordance with the present invention includes a data processing system arranged to receive data derived from each of a plurality of microsensor units which contain the corrosion sensors, to process the detection data and to provide corrosion analysis data based thereon, whereby corrosion state prediction is provided for the bulk alloy materials of the various different components in the various different locations being monitored. The units include a battery and a sensing circuit for each sensor. In the case of the LPR sensor, the circuit is adapted to apply a constant current to common terminals of the sensor, and to measure a voltage generated therein to sense resistance changes in the sensor. In the case of the galvanic sensor, the circuit is adapted to sense the galvanic voltage generated across the two common terminals.

One or more of the corrosion sensors of the present invention may be included in a semi-autonomous microsensor unit which includes a data logging memory, for storing sensor data sensed at a plurality of intervals over a period of time, and a data output whereby data is output from the microsensor unit to the data processing system. Such a semi-autonomous microsensor unit may be connected to the data processing system by means of physical wiring trough which data is communicated, or may include a data port whereby a data connection is intermittently established. The data port may be a socket to which a data cable of a reader unit is manually connected, or a wireless data port such as a Bluetooth™ short range radio transmitter.

The above embodiments are to be understood as illustrative examples of the invention. Further embodiments of the invention are envisaged. Note for example that, whilst the corridors across which the corrosive tracks extend are in the above-described embodiments linear, the corridors may instead take a different form, including various different curved forms, including bell-shaped forms. Whilst in the above embodiments, all of the conductive thin film parts of each of the corrosion sensors are formed on a single substrate in an alternative configuration the microsensor includes conductive thin film parts of each of the different sensors which are formed on a plurality of different substrates, which may be bonded together.

Using thin film alloys to mimic the behaviour of bulk alloys lends itself to further applications in corrosion both to elucidate corrosion rates specific to specific components and locations thereon, in which the microsensor is mounted. It should be noted that the invention is applicable to alloy systems other than aluminium, including magnesium alloys, which are used in the manufacture of gearbox components. It has particular benefit for alloys which tend to corrode locally, such as by exfoliation, or intergranular, pitting, crevice or stress corrosion.

It should be understood that the above-described preferred geometries, in particular the track width values, the track section separation values and the minimum radii of curvature values, have been found by empirical observation. Experiments were conducted in which the corrosion rates of large numbers of different test geometries were compared with the corrosion rates of the bulk metal materials being mimicked, when exposed to the same corrosive media. Geometries inside or outside the thresholds described were found to tend to cause corrosion effects which did not accurately reflect those in the bulk material; however it should be understood that, if different sensor characteristics are desired, for example increased sensitivity to corrosion relative to the bulk material, such alternative geometries may be used.

It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

The invention claimed is:

1. A microsensor for detecting corrosive media acting on a metallic material when mounted in situ adjacent a location in the metallic material, said microsensor comprising a plurality of resistivity sensors, each sensor having at least one patterned conductive thin film track arranged to provide a measurable variation in resistivity in response to corrosion exposure, each sensor providing a different indication of corrosion than another of said sensors, wherein the resistivity sensors include a first resistivity sensor having said at least one thin film track of a first width and a second resistivity sensor having said at least one thin film track of a second, different width, said microsensor providing a separate output derived from each of said sensors, wherein said second width is a tenth or less of the first width.

2. A microsensor according to claim 1, wherein the plurality of resistivity sensors include a resistivity sensor having at least one thin film track of a first thickness and a resistivity sensor having at least one thin film track of a second, different thickness.

3. A microsensor according to claim 1, wherein the plurality of resistivity sensors include a resistivity sensor having at least one thin film track made of a first metallic composition and a resistivity sensor having at least one thin film track of a second, different metallic composition.

4. A microsensor according to claim 1, wherein the plurality of resistivity sensors include a resistivity sensor having at least one thin film track having a first surface type and a different resistivity sensor having at least one thin film track of a second, different surface type.

5. A microsensor according to claim 1, further including a galvanic sensor having at least one thin film track made of a first metallic material and at least one further thin film track made of a second, different, metallic material, the tracks being arranged to provide a measurable variation in galvanic voltage in response to exposure to an electrolyte.

6. A microsensor according to claim 1, wherein the plurality of resistivity sensors include a resistivity sensor and a reference sensor arranged to provide a measurable variation in resistivity in response to changes in temperature, the reference sensor having similar temperature dependence to said resistivity sensor.

7. A microsensor according to claim 1, comprising a resistance thermometer sensor arranged for measuring temperatures in an area in which the microsensor is mounted.

8. A microsensor according to claim 1, comprising an airflow sensor arranged for measuring levels of airflow in an area in which the microsensor is mounted.

9. A microsensor according to claim 1, wherein all of the conductive thin film parts of each of the corrosion sensors are formed on a single substrate having a surface formed from an insulating material.

10. A corrosion sensing system comprising a microsensor according to claim 1, wherein said system includes a data processor arranged to receive data derived from each of said separate outputs, to process said detection data and to provide corrosion analysis data based thereon.

11. A microsensor for detecting corrosive media acting on a metallic material when mounted in situ adjacent a location in the metallic material, the microsensor including a plurality of different corrosion sensors, each said sensor having at least a part formed from a patterned conductive thin film and the different sensors being arranged to be differently influenced by corrosive media in an area in which the unit is mounted, said microsensor providing a separate output derived from each of said sensors respectively, wherein the plurality of corrosion sensors comprise a resistivity sensor having at least one thin film track arranged to provide a measurable variation in resistivity in response to prolonged exposure to corrosive media, wherein the plurality of corrosion sensors comprise a plurality of resistivity sensors each having at least one thin film track arranged to provide a measurable variation in resistivity in response to prolonged exposure to corrosion, wherein the resistivity sensors include a first resistivity sensor having said at least one thin film track of a first width and a second resistivity sensor having said at least one thin film track of a second, different width, wherein said second width is a tenth or less of the first width.

* * * * *